(12) United States Patent
Olson, Jr.

(10) Patent No.: US 7,172,558 B2
(45) Date of Patent: Feb. 6, 2007

(54) DEVICE FOR CONTAINING AND ANALYZING SURGICALLY EXCISED TISSUE AND RELATED METHODS

(75) Inventor: John A. Olson, Jr., Chapel Hill, NC (US)

(73) Assignee: Duke University, Durham, NC (US)

( * ) Notice: Subject to any disclaimer, the term of this patent is extended or adjusted under 35 U.S.C. 154(b) by 432 days.

(21) Appl. No.: 10/429,518

(22) Filed: May 5, 2003

(65) Prior Publication Data
US 2004/0224382 A1    Nov. 11, 2004

(51) Int. Cl.
*A61B 5/00* (2006.01)
(52) U.S. Cl. .................................. 600/562; 604/317
(58) Field of Classification Search ................ 600/562; 604/317, 403; 422/102
See application file for complete search history.

(56) References Cited

U.S. PATENT DOCUMENTS

| | | | | |
|---|---|---|---|---|
| 2,837,055 | A * | 6/1958 | Whitehead | 118/500 |
| 3,195,502 | A * | 7/1965 | Levy | 118/500 |
| 3,554,433 | A * | 1/1971 | Cardenaz | 229/235 |
| 4,220,252 | A * | 9/1980 | Beall et al. | 422/102 |
| 4,591,445 | A * | 5/1986 | Spinell et al. | 210/781 |
| 4,837,795 | A * | 6/1989 | Garrigus | 378/180 |
| 4,993,056 | A | 2/1991 | Lary | |
| 5,002,735 | A | 3/1991 | Alberhasky et al. | |
| 5,383,472 | A | 1/1995 | Devlin et al. | |
| 5,427,742 | A * | 6/1995 | Holland | 422/102 |
| 5,568,534 | A * | 10/1996 | Watkins | 378/208 |
| 5,609,827 | A | 3/1997 | Russell et al. | |
| 5,817,032 | A | 10/1998 | Williamson, IV et al. | |
| 6,225,107 | B1 | 5/2001 | Nagle | |
| 6,899,850 | B2 * | 5/2005 | Haywood et al. | 422/102 |
| 6,904,916 | B2 * | 6/2005 | Bakane | 128/885 |
| 6,991,934 | B2 * | 1/2006 | Walton et al. | 435/307.1 |

* cited by examiner

*Primary Examiner*—Max Hindenburg
(74) *Attorney, Agent, or Firm*—Jenkins, Wilson, Taylor & Hunt, P.A.

(57) ABSTRACT

A collection device and method of use for excised tissue immobilization, removal of core samples from immobilized tissue and transport of the tissue for specimen radiography and pathological analysis. The collection device is comprised of a base member having an annular bottom wall and a side wall upwardly extending from the peripheral edge of the side wall, a lid member having a top wall and a skirt circumscribing the side wall and extending downwardly therefrom, and an incremental latching mechanism for securing the lid member to the base member. The side wall of the lid member includes a plurality of apertures positioned around at least a portion of the circumference of the side wall. In use, a tissue specimen placed in the base member is immobilized by compressing the tissue between the top wall of the lid member and the bottom wall of the base member and securing the lid member and base member together with the latching mechanism. A core sample can be removed from the immobilized specimen by inserting a portion of a sampling device through an aperture. The remainder of the specimen can be transported as needed for pathological or radiographic analysis.

25 Claims, 3 Drawing Sheets

DEVICE FOR CONTAINING AND ANALYZING SURGICALLY EXCISED TISSUE AND RELATED METHODS

TECHNICAL FIELD

The present invention relates to devices for containing tissue specimens, and more particularly to devices that provide for the containment, immobilization, core sampling, transport, analysis, and storage of surgically excised tissues, particularly tissues containing suspected tumor masses, and methods related to using the devices.

BACKGROUND ART

Cancer is the second leading cause of death in the U.S. after heart disease. The American Cancer Society predicts that more than 1.3 million new cancers will be diagnosed in 2003. This prediction does not even include non-invasive cancers and basal and squamous cell skin cancers. It is predicted that over 500,000 Americans will die from cancer this year alone.

Tremendous effort and resources are directed toward diagnosing and treating cancer. More than half of all cancers are susceptible to screening and early detection procedures, with resultant increases in survivability. It is estimated that if all cancers amenable to screening were detected in their early stages, survivability would increase to around 95%.

Diagnosis and treatment of cancer has progressed tremendously over the past several years. At one time, diagnosis of a tumor as "benign" or "malignant" was believed sufficient for a physician to plan and implement a course of treatment. However, cancer is not a single disease that responds well to a single treatment regimen. There are more than 300 distinctly identified types of tumors. Further, tumors have a course of development, a "maturing process", and therefore it is also important to identify at what stage of growth the tumor is for predicting outcome and choosing the proper treatment strategy. Options for therapy have also greatly increased in recent years with regimens more directly tailored for specific types of tumors at particular stages of development. Therefore, it is more important than ever to have detailed information about an identified tumor in order to achieve the best outcome for a patient.

Using techniques of gross and microscopic examination of excised tissue, surgical pathologists play a vital role in gathering the information about type and stage of a tumor needed by a physician to plan a treatment course for the patient. Recent advances in molecular pathology related to a greater understanding of the specific genetic changes cells undergo to become cancerous promises to provide valuable information useful for designing treatment courses that are better tailored to the particular needs of an individual patient. This will provide a greater chance of survivability with less side effects and unnecessary suffering for the patient. For example, presently, if a mass is discovered in the breast of a patient, the mass is often surgically excised and analyzed to determine if it is cancerous. If so, the preferred course of treatment is often chemotherapy, which can have severe side effects. However, studies suggest that only 10% of patients treated with chemotherapy actually benefit from the treatment. Therefore, up to 90% of those undergoing chemotherapy may be suffering the side effects needlessly. Unfortunately, it is necessary, since gross and microscopic pathological analysis of the tumor cannot differentiate which patients will or will not benefit from the treatment.

As our understanding of the underlying genetic mechanisms of specific cancers increases, molecular pathological analysis of tumors will provide additional information to a physician so that a treatment regimen better tailored to the specific needs of an individual patient can be developed. This will increase chances for a positive outcome and decrease unnecessary suffering due to side effects.

Molecular pathology now plays a small role in identifying tumors and planning treatment strategies, however, this will undoubtedly change as more information about the underlying genetics of tumors comes to light. In the very near future, it will become necessary to divert portions of excised tumors for molecular testing.

At present, a majority of the demand for tumor samples related to molecular pathology is in basic and applied research directed at linking genetic findings to clinically observed pathology. Sources of tumor tissue for research are generally limited to tumor banks. Although these banks have been an immensely valuable source of materials and information for molecular analysis of tumors, for a number of reasons, the amount of useful data that can be collected is limited. First, a majority of the tissue found in tumor banks is from large tumors. Since genetic expression changes during different stages of tumor development, testing of larger tumors only does not provide a complete picture of tumor "lifecycles". Furthermore, clinical screening for tumors in patients is becoming more precise, and therefore a greater majority of tumors found are smaller, and thus poorly represented by tumor bank specimens.

Second, the tissue is preserved, and so the amount of time lapsed between harvesting the tissue and preserving it is often unknown. Gene expression can change after removal of tissue from a patient as cells become anoxic and shift metabolism or even begin a shutdown of cell function. Thus, analysis of tissue aged prior to study may present a genetic expression profile greatly altered from what is found in a tumor intact in a patient. Also, preservation methods and reagents can adversely affect expressed proteins in the sample cells and obscure data.

Rather than rely on samples from tumor banks, tissue can instead be collected after gross and microscopic pathological analysis of a specimen. Again, however, significant time may pass between excision of the tissue and molecular testing to know the results are trustworthy. Thus, it is preferable to perform molecular analysis on tissue within minutes after excision of the tumor or on tissue immediately frozen after excision.

Although it is preferable to perform molecular analysis on tissue immediately after excision of a tumor, scientific progress should not come at the detriment of the immediate needs of the individual patient. Collection of tissue from a newly excised tumor could result in a loss of structural integrity of the tumor, thus preventing proper pathological analysis needed to classify the tumor type and stage. Further, a long delay between excision of the tumor and pathological analysis due to sampling tissue for molecular analysis could adversely affect the patient as well. Also, transfer of the tissue between too many hands could corrupt the integrity of the specimen, create a biohazard risk, and bring the results of the pathological analysis into question.

Accordingly, there is a long-felt need for a device for collecting small tissue specimens from suspected tumors immediately after excision from the patient for molecular analysis that is easy and safe enough to be used by operating room personnel immediately upon excision and in such a way that the pathologist receiving the tumor knows with accuracy from where the specimen was taken. The sampling device must not significantly alter the tumor structure so as to compromise the gross and microscopic pathological analysis. Most suitably, the device should maintain the specimen in the exact orientation in which it resided when it was removed from the patient. This ensures that the radiologist can better determine the location of a mass within the sample or that the pathologist can accurately determine margins and better direct the surgeon, should further excision of tissue be required in order to remove the entire suspect region of tissue.

The prior art discloses a variety of devices available for securing and transporting excised tissues for pathologic and/or radiologic evaluation. For example, tissue samples can be sandwiched between two plates, with the plates forming a grid for locating a mass within a tissue sample during subsequent radiological and pathological evaluation, as taught in U.S. Pat. No. 5,002,735 to Alberhasky et al. Although this device immobilizes the specimen, it does not prevent fluids from leaking since the sides of the carrier are open. Further it does not provide a means for sampling the tissue immediately after excision and immobilization without removing one of the plates. U.S. Pat. No. 6,225,107B1 to Nagle also discloses a device for immobilizing an excised specimen comprising an outer box with an open end and an inner box that is sized to slidingly insert into the open end of the outer box. The specimen is first inserted into the outer box and then compressed to a fixed position when the inner box is inserted into the open end of the outer box. This device does not provide for a means of sampling the tissue after immobilization. Further, the only means of securing the tissue in place is by a cumbersome technique of suturing the two boxes together. Neither of the prior art devices have a geometric conformation ideally suited for sampling of the tissue contained within from any angle, regardless of how the specimen is positioned.

Therefore, there is a long-felt need for a device for securing an excised tissue in a fixed position, for transport, radiography and pathological analysis, while also facilitating collection of samples for molecular analysis immediately after excision without destroying structural integrity of the specimen. Applicants have invented such a device.

SUMMARY OF THE INVENTION

The invention is directed to a collection device for excised tissue immobilization and transport for radiography and pathological analysis. The device is further used to facilitate removing small core samples from the immobilized tissue immediately after excision without damaging the structural integrity of the excised tissue or moving it from its original immobilized position.

The collection device includes a base member, a removable annular lid member adapted to be matingly fitted to the base member, and at least one incremental latching mechanism for securing the lid member to the base member after a collected tissue specimen is placed in the base member. The base member has an annular bottom wall and a side wall extending up from the peripheral edge of the base member for containing the collected tissue specimen. The side wall has a plurality of apertures positioned around at least a portion of the circumference of the side wall. Apertures facilitate selected core sampling of the tissue therethrough. The lid member has a top wall with a skirt circumscribing the top wall and extending downward therefrom. The incremental latching mechanism facilitates immobilizing the tissue in the collection device by allowing the user to apply continuous selected compression pressure to the tissue specimen by compressing it between the lid member and the base member and then securing the latching mechanism.

In another embodiment, the collection device of the present invention may further include a notch within an upper edge of the side wall. The notch can support a guide wire positioned within the collected tissue specimen. This further aids in immobilizing the tissue specimen.

In another embodiment of the present invention, the collection device may include a plurality of generally vertically extending slits through the skirt thereof. The slits are positioned such that each of the slits aligns with a corresponding one of the apertures when the lid member is matingly fitted to the base member.

In yet another embodiment of the present invention, one or more of the inner surfaces may be textured so as to aid in immobilizing the specimen when the lid member is matingly fitted to the base member and compression force applied. In one aspect, the bottom wall has a textured inner surface. In another aspect, the inner surface of the top wall is textured. In yet another aspect, both the top and bottom walls are textured. Also, one or more of the textured surfaces can be in the form of orientation lines for localizing specific points on the collected tissue. Alternatively, the orientation lines can be in lieu of the textured surfaces or separate from but in addition to the textured surfaces. In order to further enhance use of the device, it may be manufactured at least partially from translucent materials so as to permit viewing of the specimen. As a matter of design choice, the device can also be manufactured at least in part of a radiolucent material for radiographically visualizing the tissue.

In yet another embodiment of the present invention, the collection device can include an incremental latching device that includes a first member and a second member wherein the first member is positioned on the side wall of the base member and the second member is positioned on the skirt of the lid member. The second member includes a flexible biasing arm with a middle section affixed to the skirt of the lid member and flanked by a first end having one or more ridges and a second end being a release lever. The first member of the latching device has a plurality of ridges that lockingly engage one or more of the ridges of the first end of the second member of the latching device. The release lever allows disengagement of the second member ridges from the first member ridges and release of the lid member from the base member.

In still another embodiment of the present invention, apertures of the collection device have a diameter sufficiently large to permit passage of the operating end of a core needle biopsy device through the aperture. This permits the user to take a core sampling of the tissue specimen in the collection device. Core sampling can be facilitated in another embodiment of the present invention wherein the longitudinal axis of each of apertures intersects the center of the base member. As a further safety feature, the present invention can include apertures spaced such that the longitudinal axis of each of the apertures does not intersect any other of the apertures, thereby preventing passage of the needle from the biopsy device through one aperture and out another aperture on the opposite side of the collection device resulting in possible injury to the hand of the user.

The invention additionally relates to methods for handling and sampling an excised tissue specimen. These methods allow use of only one device for collection, core sampling and transport of the tissue without need for opening the device or moving the tissue once it is immobilized in the device. The method comprises surgically excising a tissue specimen from a subject, securing the tissue specimen in a fixed position in the collection device, removing a core biopsy tissue sample for molecular analysis from the tissue specimen and analyzing the tissue specimen, less the core biopsy sample, using pathological procedures.

The present invention further includes methods of using a collection device for holding a tissue specimen containing a suspected tumor mass embedded within normal tissue. These methods can further comprise radiographically locating the suspected tumor prior to excising it and marking the suspected tumor with a radiopaque marker. The marker can be any of a number of conventional elements, including a guide wire.

The present invention still further encompasses methods that include subjecting the tissue specimen to radiography to ascertain the location and position of the suspected tumor mass after securing the tissue specimen in a fixed position in the collection device.

The present invention further includes a method for handling and sampling a tissue specimen comprising the steps of surgically excising a tissue specimen from a subject, compressibly securing the tissue specimen in a fixed position in an annular collection device having a plurality of spaced apart apertures around at least a portion of the circumference of the annular collection device, inserting a core needle biopsy device through a selected aperture, removing a core biopsy tissue sample for molecular analysis from the tissue specimen with the core needle biopsy device, and analyzing the tissue specimen less the core biopsy sample using pathology procedures. The method may further include using a collection device comprising a base member having an annular bottom wall and a side wall upwardly extending from the peripheral edge of the bottom wall for containing the tissue specimen. The side wall has a plurality of spaced apart apertures around at least a portion of the circumference of the side wall to facilitate selected core sampling of the tissue specimen therethrough. The collection device includes a removable annular lid member adapted to be matingly fitted to the side wall of the base member. The lid member has a top wall and a skirt circumscribing the top wall and extending downward therefrom. The collection device has at least one incremental latching mechanism for securing the lid member to the base member when the tissue specimen is compressibly secured in a fixed position.

Further still, the method of the present invention may include a step of compressibly securing the tissue specimen in a fixed position that includes placing the tissue specimen in the base member, matingly fitting the lid member onto the base member, applying downward force on the lid member to compress and immobilize the tissue specimen between the lid member and the base member, and engaging the incremental latching mechanism to secure the lid member to the base member and hold the tissue specimen in a fixed position.

Some of the objects of the invention having been stated hereinabove, and which are addressed in whole or in part by the present invention, other objects will become evident as the description proceeds when taken in connection with the accompanying drawings as best described hereinbelow.

DETAILED DESCRIPTION OF THE INVENTION

Figure 1:
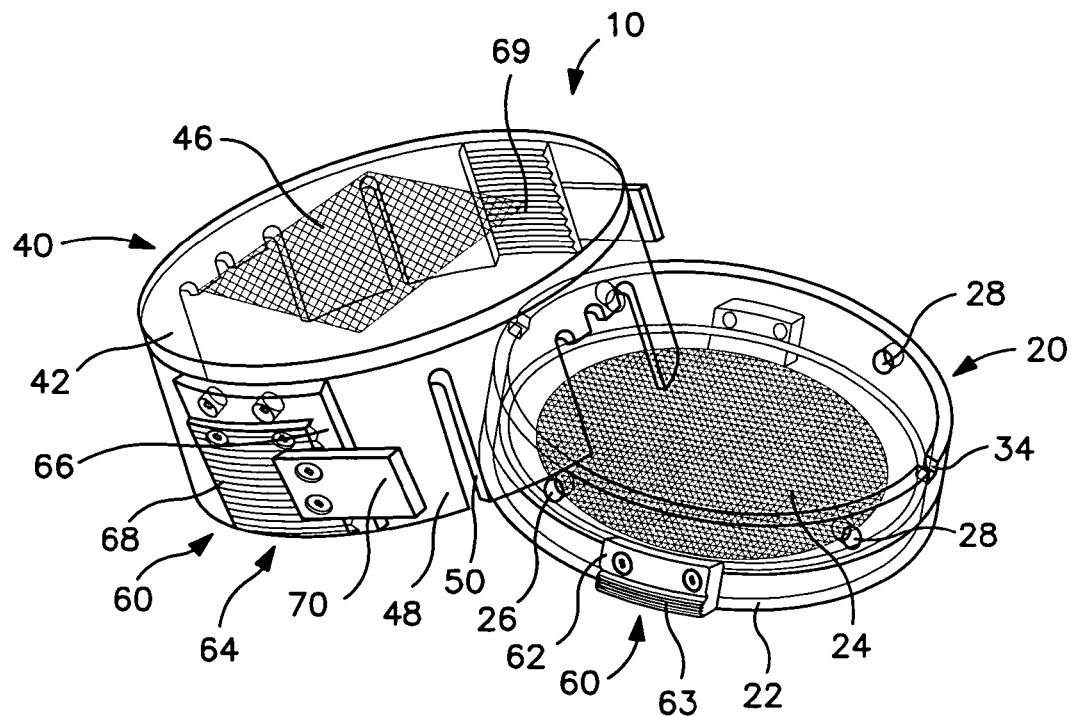
FIG. 1 is a perspective view of the disassembled tissue collection device of the present invention.
Figure 2:
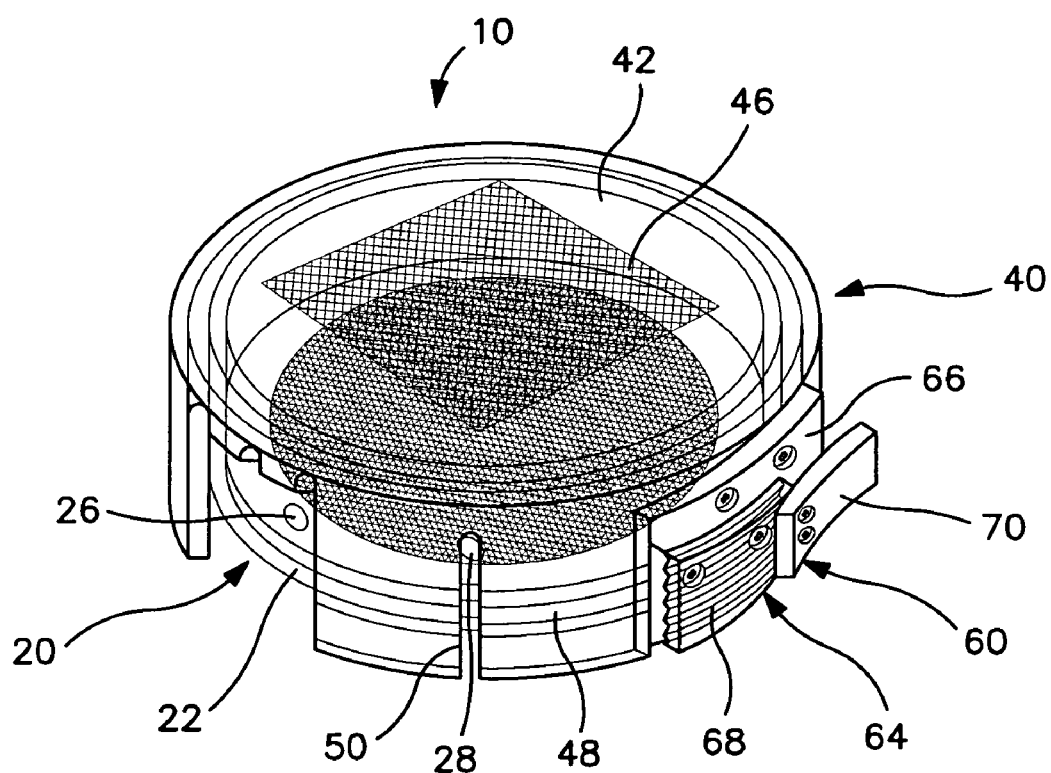
FIG. 2 is a perspective view of the assembled tissue collection device of the present invention as shown in FIG. 1.
Figure 3:
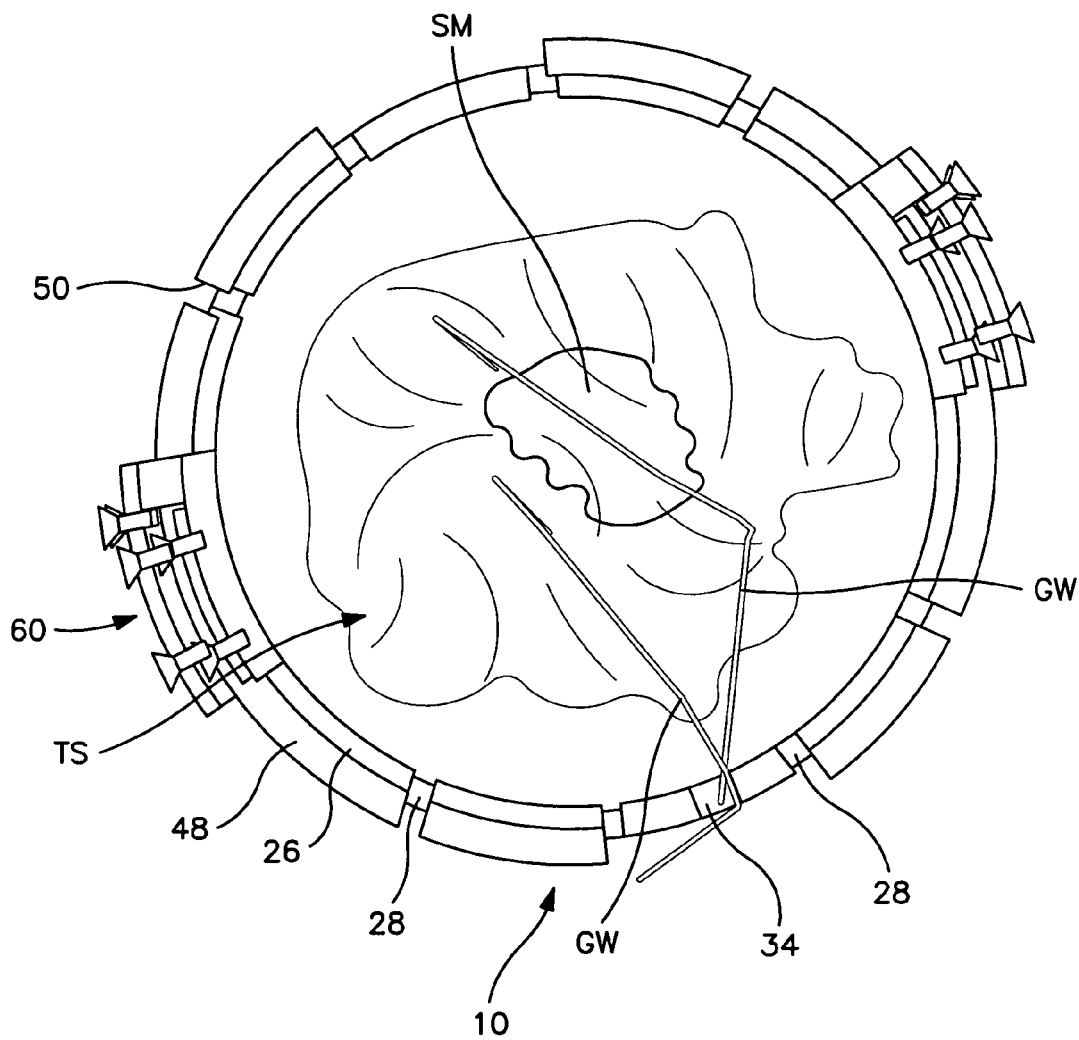
FIG. 3 is a radiograph (top plan view) of the assembled tissue collection device of the present invention containing a tissue specimen with a suspected tumor mass at its center and further containing guide wires in the specimen marking the suspect region of the tissue specimen.

As shown in FIGS. 1–3, a collection device 10 for containing and immobilizing a surgically excised tissue specimen TS is disclosed. The collection device 10 functions to permit core sampling of tissue specimen TS for molecular or similar analysis without requiring shifting or relocation of immobilized tissue specimen TS. Collection device 10 containing the remainder of tissue specimen TS can then be used as a transport and storage device for specimen TS as it undergoes radiographic and/or pathological analysis. The excised tissue specimen TS may be a surgically or otherwise excised specimen suspected of being abnormal and therefore requiring further diagnostic or therapeutic evaluation or examination, such as, but not limited to, tissue containing a tumor, lesion, cyst or mass of cell. Collection device 10 of the present invention is particularly well suited for containing such specimens undergoing multiple forms of analysis, in particular, specimens where it is desirable to perform both molecular analysis on core samples removed from tissue specimen TS and radiographic and/or pathological analysis of the remaining specimen mass.

As best seen in FIGS. 1 and 2, collection device 10 of the present invention includes a base member 20 and a lid member 40 adapted to be matingly fitted to the base member 20. An incremental latching mechanism 60 secures the lid member 40 to the base member 20.

The base member 20 includes an annular bottom wall 22 and a side wall 26 extending upwardly from the peripheral edge of bottom wall 22. Side wall 26 has a plurality of apertures 28 positioned around at least a portion of the circumference of the side wall 26. Side wall 26 preferably also has one or more notches 34 in the upper edge thereof. Apertures 28 facilitate selected core sampling of tissue specimen TS contained within collection device 10. It is envisioned that device 10 of the present invention will be used in conjunction with a sampling device, such as a core needle biopsy device, for sampling a core of tissue from specimen TS. Examples of devices suitable for use with collection device 10 of the present invention include handheld and spring-loaded core needle biopsy devices such as a BIOPTY GUN available from Bard of Covington, Ga. and a BIOPINCE available from Amedic of Sollentuna, Sweden.

In one embodiment of device 10 of the present invention, apertures 28 are positioned equidistant from one another around the entire circumference of side wall 26. This arrangement ensures that the most proximal access can be gained to tissue specimen TS regardless of where specimen TS is positioned in collection device 10. Apertures 28 preferably have an annular shape, however the present invention is not limited to this configuration and may also include other geometric forms, including but not limited to, square, rectangular, octagonal or circular forms. In device 10 shown in FIG. 1, apertures 28 are elliptical in shape. This permits some vertical motion of the core sampling device during core sampling. The diameter of each aperture 28 is large enough to accommodate passage of the operating end of the core sampling device. For example, if a core needle biopsy device is used, each aperture 28 will have a diameter sufficiently large enough for the coring needle of the biopsy device to pass through it with enough extra space for the needle to be maneuvered to direct the needle end to the portion of the tissue specimen TS that is to be sampled. Preferably, each of apertures 28 is large enough to accommodate the operating end of an 11-gauge core needle biopsy device and each aperture 28 is formed such that the longitudinal axis of the aperture intersects the center of the base member 20. This arrangement further aids in guiding the operating end of the sampling device toward the center of tissue specimen TS, where it is most likely the suspicious mass SM resides. Further, apertures 28 may be arranged such that the longitudinal axis of each of apertures 28 does not intersect any other aperture 28. This provides an additional safety feature for the user. If none of apertures 28 are positioned directly across from others on side wall 26, the user is less likely to accidentally force a core sampling needle completely through the tissue sample and out through an opposing aperture, thereby creating a needle-stick risk to the user.

Referring to FIG. 3, notch 34 serves as a support for a radiopaque marker, such as a guide wire GW, positioned within and extending from tissue specimen TS when specimen TS is contained within collection device 10. More than one notch 34 may be beneficial if tissue specimen TS has several guide wires GW projecting at different angles from specimen TS.

Referring again to FIGS. 1 and 2, lid member 40 includes a top wall 42 and a skirt 48 circumscribing the top wall 42 and extending downward therefrom. As shown in FIG. 2, lid member 40 is adapted to be matingly fitted to side wall 26 of base member 20. When lid member 40 is matingly fitted onto base member 20, skirt 48 engages the outer surface of side wall 26 and seals the inner area of collection device 10. This aids both in securing specimen TS in position while also containing fluids and preventing unnecessary contact between specimen TS and the outside environment. In this manner, collection device 10 serves not only as a tool for immobilizing specimen TS for analysis, but also as a vessel for transport, radiographic imaging and storage of specimen TS.

Skirt 48 may further include a plurality of generally vertically extending slits 50 therein. As best shown in FIG. 2, slits 50 are positioned such that when lid member 40 is matingly fitted to base member 20, each of slits 50 aligns with a corresponding one of apertures 28. This arrangement permits access to specimen TS through apertures 28 and slits 50 when lid member 40 is fitted to base member 20. Thus, even after collection device 10 is closed, a core sample of specimen TS can be collected without disturbing the arrangement of specimen TS in collection device 10.

The latching mechanism 60 of the present invention can take several forms. It functions to secure lid member 40 to base member 20 after tissue specimen TS is placed in collection device 10 and facilitates immobilizing specimen TS in a desired orientation. The latching mechanism 60 may simply be a latch and hook mechanism, or it may have a more complicated structure. Immobilization of tissue specimen TS requires compression of tissue specimen TS between top wall 42 of lid member 40 and bottom wall 22 of base member 20. However, tissue specimen TS thickness will vary, and therefore it is desirable to be able to apply varying amounts of compression to a specimen TS using collection device 10. The latching mechanism 60 can facilitate this incremental compression of tissue specimen TS. In one embodiment, as shown best in FIGS. 1 and 2, latching mechanism 60 is an incremental latching mechanism. The mechanism allows for locking lid member 40 to base member 20 wherein the vertical distance between bottom wall 22 of base member 20 and top wall 42 of lid member 40 may be incrementally adjusted in order to apply the proper amount of compression to each individual tissue specimen TS.

Figure 1A:
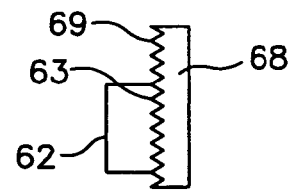
FIG. 1A is a vertical cross-sectional view of the latching mechanism of the tissue collection device of the present invention.

The incremental latching mechanism 60, as best shown in FIG. 1, includes a first member 62 located on side wall 26 of base member 20 and a second member 64 located on skirt 48 of lid member 40. First member 62 includes a plurality of ridges 63 that second member 64 can engage. Second member 64 is a flexible biasing arm that has a medial section 66 affixed to skirt 48. The medial section 66 is flanked by a first end 68 and a second end 70. As shown in FIG. 1a, first end 68 has one or more ridges 69 on the bottom thereof that lockingly engage ridges 63 on the outside of first member 62 when lid member 40 is matingly fitted to base member 20. Second end 70, adjacent of medial section 66, is a release lever that when pressed by the user biases first end 68 of second member 64 away from first member 62 and thus disengages first end ridges 69 from first member ridges 63. This acts to release lid member 40 from base member 20.

For a user, when engaging incremental latching mechanism 60, downward force is applied to the lid member 40 seated on base member 20 until the desired compressional force is exerted on specimen TS. Latching mechanism 60 automatically engages and releases incrementally as further downward force is applied to lid member 40. However, latching mechanism 60 will not release in response to upward force unless second end release lever 70 of latching mechanism 60 is depressed with sufficient force to release ridges 69 thereof from ridges 63 of first member 62. Thus, downward force is maintained on specimen TS, immobilizing it, until the user desires to release lid member 40 from base member 20.

Of course, it should be recognized that other suitable latching mechanisms would facilitate application of the desired incremental compression to tissue specimen TS and that the present invention is intended to encompass these mechanisms as well. As one example, a hook and eye fastening mechanism would be a suitable alternative latching mechanism.

The bottom wall 22 of base member 20 can have texturing 24 on its inner surface to increase its coefficient of friction and assist in immobilizing tissue specimen TS when it is compressed between bottom wall 22 and top wall 42. Suitable texturing 24 includes, but is not limited to, spikes, ribs, nubs or grooves arranged randomly or in particular patterns (for example, a textured grid 24, as is shown in FIGS. 1 and 2). Similar texturing 46 (see FIG. 2) may also be included on the inner surface of top wall 42 either in lieu of texturing 24 on bottom wall 22, or in combination with it. Texturing on top wall 42 or bottom wall 22 can also serve as an orientation system for geographically locating landmarks or features of specimen TS, or to indicate where a core sample was removed. For example, as shown in FIGS. 1 and 2, the texturing 46 is arranged as raised intersecting lines forming a grid pattern on the inside of top wall 42 of lid member 40. This grid texturing 46 can have coordinate labeling on the edges, thus providing an easy system for noting particular regions of the immobilized specimen TS contained within and for guiding tissue biopsy. In addition or in lieu of this coordinate system, alternative arrangements such as a plurality of raised concentric circles, or other related coordinate systems could be used. The coordinate system may also be located on the outer surface of lid member 40, therefore functioning independently of texturing 46, if so desired.

While an annular shaped container is preferred for ease of access to specimen TS for core sampling, collection device 10 is not limited to this shape and may be, for example, square, rectangular or any other geometric shape. Collection device 10 is circular in a preferred embodiment. This design facilitates ease of access to the tissue specimen TS, regardless of where it is positioned within the collection device 10, and will generally track the perimeters of tissue specimen TS, as it tends to have an annular shape. The lid member 40 and base member 20 are shown here as being completely separable, but they may also form a unitary device with lid member 40 and base member 20 connected by, for example, a hinge or other flexible connector.

In one embodiment, a series of different size collection devices 10 are available to accommodate various sized specimens TS. A surgeon or practitioner then selects the collection device 10 that is sized to either just accommodate a specimen TS or to contain a smaller-sized specimen TS. Collection device 10 of the present invention is preferably sized to encompass specimens TS ranging in size from about 3 cm to about 9 cm. The collection device 10 may range in size from about one to about five times the size of specimen TS size. In a preferred arrangement, bottom wall 22 of base member 20 has a diameter of from about 3 cm to about 12 cm and side wall 26 has a height from about 1 cm to about 3 cm.

The collection device 10, or at least a portion of collection device 10, such as top wall 42 or bottom wall 22, or both, may be made of a material that is either optically or radiographically transparent, or both. Examples of such transparent materials are polymeric materials and polymeric materials that have been reinforced with glass or carbon for increased strength and resistance to puncture or breakage. It is also desirable that collection device 10 be made of a material that is resistant to high temperatures and pressures so that it can be sterilized by steam autoclave. Device 10 is preferably intended to be a disposable item designed for single use.

In use, a suspect tissue specimen TS is excised from the body and is placed in base member 20, preferably in the exact orientation in which it was located in the body and then removed from the body. If a guide or localization wire GW is present, it is oriented so that it exits from notch 34 in side wall 26. The tissue specimen TS frequently is suspected of containing or may in fact be known to contain a tumor, mass, lesion, or cluster of suspicious or abnormal cells 82. Specimen TS may be, for example, breast tissue obtained by excision preceded by insertion of a marker, such as a guide wire GW, for example, a Kopans localization needle, under mammographic guidance for localization of an impalpable abnormal shadow or microcalcification (needle localization biopsy), lumpectomy of a defined or palpable mass or from a partial or total mastectomy. The invention is not limited to this procedure, however. For example, in cases where the mass SM is palpable, a guide wire GW and mammography will not be required. The method and device are also not limited to use with breast tissue specimens and may be used with any excised solid tissue specimen, preferably one requiring multiple forms of analysis, such as a cyst or a solid organ specimen, for example, a lung or liver biopsy specimen.

The tissue specimen TS is immobilized in collection device 10 by matingly fitting lid member 40 to base member 20 and applying a downward force on lid member 40 to compress and immobilize tissue specimen TS between top wall 42 of lid member 40 and bottom wall 22 of base member 20. In order to maintain tissue specimen TS in its fixed position, latching mechanism 60 is engaged, either automatically or manually, depending on the particular latching mechanism 60.

It may be desirable to obtain a radiogram of specimen TS in collection device 10 using radiography in order to ascertain the location and position of suspected mass SM within tissue specimen TS. Generally, radiography means placing collection device 10 containing specimen TS between an x-ray source and radiographic film and exposing the film and collection device 10 to x-rays. If this is desired, it is important that collection device 10 be manufactured from a radiolucent material. As shown in FIG. 3, the radiograph shows clearly the location of suspected mass SM in relation to entire specimen TS, the guide wires GW and collection device 10. The radiograph assists the practitioner in determining where within specimen TS it is most desirable to remove a core sample and which apertures 28 are most proximal to suspected mass SM. If it is not possible to obtain a radiograph of specimen TS within collection device 10, then core samples are taken through apertures 28 proximal to guide wire GW, or even through notch 34, working around guide wire GW.

After immobilizing specimen TS within collection device 10, a core biopsy tissue specimen can be taken from the specimen very soon after excision from the patient and prior to gross and microscopic pathological analysis. In order to take a core specimen, the operating end of a needle biopsy device (such as a spring-loaded or hand-held core needle biopsy device containing an 11–14 gauge needle) is inserted through a selected aperture 28, preferably one proximal to the tissue specimen. Specimen TS is contacted with the biopsy device and pierced. The core sample is then extracted into the biopsy device and removed from collection device 10 for molecular or other studies. Additional core samples can be removed from specimen TS if desired. The location from which the core sample was taken can be noted for future reference either by marking the aperture used or noting the coordinates from the grid lines, if present on top wall 42 of lid member 40. The remainder of specimen TS is then sent to the pathology lab, including notation of where the core sample was removed, for standard identifying pathology procedures.

Collection device 10 of the present invention permits rapid core sampling of excised tissue specimens TS while still in the operating theater without added difficulty to the surgical team or compromise to specimen TS that would prevent proper analysis and identification by a pathologist. It is anticipated that using collection device 10 and the methods outlined above, a core sample can be collected from a tissue specimen TS within five minutes of its excision from a patient. This ensures that subsequent molecular analysis of the fresh core samples will provide the accurate data required for both research and clinical needs.

It will be understood that various details of the invention may be changed without departing from the scope of the invention. Furthermore, the foregoing description is for the purpose of illustration only, and not for the purpose of limitation, as the invention is defined by the claims as set forth hereinafter.

What is claimed is:

1. A collection device for excised tissue immobilization, core sampling of the tissue, and transport of the tissue for pathological analysis, comprising:
    (a) a base member having an annular bottom wall and a side wall upwardly extending from the peripheral edge of said bottom wall for containing a collected tissue specimen, said side wall having a plurality of apertures positioned around at least a portion of the circumference of said side wall to facilitate selected core sampling of said tissue specimen therethrough;
    (b) a removable annular lid member adapted to be matingly fitted to said side wall of said base member, said lid member having a top wall and a skirt circumscribing said top wall and extending downward therefrom, said skirt having a plurality of generally vertically extending slits therein and said slits positioned such that each of said slits aligns with a corresponding one of said apertures when said lid member is matingly fitted to said base member; and
    (c) at least one incremental latching mechanism for securing said lid member to said base member when said tissue specimen is placed in said base member and applying a selected compression to said tissue specimen to securely contain said tissue specimen between said lid member and said base member.

2. The collection device of claim 1, said side wall having at least one notch in an upper edge of said side wall for supporting a guide wire positioned in said collected tissue specimen held within said collection device.

3. The collection device of claim 1, said bottom wall having a textured inner surface.

4. The collection device of claim 3, said top wall having a textured inner surface.

5. The collection device of claim 4, said textured inner surface of said top wall defining a plurality of raised concentric circles.

6. The collection device of claim 3, said top wall of said lid member having one or more orientation lines on the outer surface of said top wall.

7. The collection device of claim 1, said incremental latching mechanism having a first member and a second member, said first member being positioned on said side wall of said base member and having a plurality of ridges, and said second member being positioned on said skirt of said lid member and having a flexible biasing arm, said flexible biasing arm having a middle section affixed to said skirt and flanked by a first end and a second end, said first end having one or more ridges that lockingly engage one or more of said base member ridges when said lid member is matingly fitted to said base member, and said second end being a release lever for disengaging said second member ridges from said first member ridges and releasing said lid member from said base member.

8. The collection device of claim 1 wherein each of said plurality of apertures has a diameter sufficiently large enough to permit passage of an operating end of an 11-gauge core needle biopsy device through said aperture.

9. The collection device of claim 8 wherein each of said apertures is directed radially inwardly such that the longitudinal axis of each of said apertures intersects the center of said base member.

10. The collection device of claim 9 wherein said longitudinal axis of each of said apertures does not intersect any other of said apertures.

11. The collection device of claim 9 wherein said plurality of apertures are spaced equidistant around the entire circumference of said side wall.

12. The collection device of claim 1, said collection device being comprised of a translucent and radiolucent polymeric material.

13. The collection device of claim 1, wherein said annular bottom wall has a diameter of from about 3 cm to about 12 cm.

14. A tissue collection device, comprising:
    (a) a base member having an annular bottom wall and a side wall upwardly extending from the peripheral edge of said bottom wall for containing a collected tissue specimen, said side wall having a plurality of apertures positioned around at least a portion of the circumference of said side wall to facilitate selected core sampling of said tissue specimen therethrough, said side wall further having at least one notch in an upper edge of said side wall;
    (b) a removable annular lid member adapted to be matingly fitted to said side wall of said base member, said lid member having a top wall and a skirt circumscribing said top wall and extending downward therefrom, said skirt having a plurality of slits, and said slits positioned such that each of said slits aligns with a corresponding one of said apertures when said lid member is matingly fitted to said base member; and
    (c) at least one incremental latching mechanism for securing said lid member to said base member when said tissue specimen is placed in said base member and applying a selected compression to said tissue specimen to securely contain said tissue specimen between said lid member and said base member.

15. The collection device of claim 14, said bottom wall having a textured inner surface.

16. The collection device of claim 15, said top wall having a textured inner surface.

17. The collection device of claim 16, said textured inner surface of said top wall defining a plurality of raised concentric circles.

18. The collection device of claim 14, said top wall of said lid member having one or more orientation lines on the outer surface of said top wall.

19. The collection device of claim 14, said incremental latching mechanism having a first member and a second member, said first member being positioned on said side wall of said base member and having a plurality of ridges, and said second member being positioned on said skirt of said lid member and having a flexible biasing arm, said flexible biasing arm having a middle section affixed to said skirt and flanked by a first end and a second end, said first end having one or more ridges that lockingly engage one or more of said base member ridges when said lid member is matingly fitted to said base member, and said second end being a release lever for disengaging said second member ridges from said first member ridges and releasing said lid member from said base member.

20. The collection device of claim 14 wherein each of said plurality of apertures has a diameter sufficiently large enough to permit passage of an operating end of an 11-gauge core needle biopsy device through said aperture.

21. The collection device of claim 20 wherein each of said apertures is directed radially inwardly such that the longitudinal axis of each of said apertures intersects the center of said base member.

22. The collection device of claim 21 wherein said longitudinal axis of each of said apertures does not intersect any other of said apertures.

23. The collection device of claim 21 wherein said plurality of apertures are spaced equidistant around the entire circumference of said side wall.

24. The collection device of claim 14, said collection device being comprised of a translucent and radiolucent polymeric material.

25. The collection device of claim 14, wherein said annular bottom wall has a diameter of from about 3 cm to about 12 cm.

* * * * *